(12) United States Patent
Dhanak et al.

(10) Patent No.: US 6,544,992 B1
(45) Date of Patent: Apr. 8, 2003

(54) UROTENSIN-II RECEPTOR ANTAGONISTS

(75) Inventors: Dashyant Dhanak, West Chester, PA (US); Steven David Knight, West Chester, PA (US); Jian Jin, West Chester, PA (US); Richard McCulloch Keenan, Malvern, PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 10/149,793

(22) PCT Filed: Dec. 19, 2000

(86) PCT No.: PCT/US00/34579

§ 371 (c)(1),
(2), (4) Date: Jun. 13, 2002

Related U.S. Application Data

(60) Provisional application No. 60/172,907, filed on Dec. 21, 1999.

(51) Int. Cl.$^7$ .................. A61K 31/5377; A61P 9/04; C07D 413/12
(52) U.S. Cl. ............... 514/235.5; 544/141; 544/372; 546/208; 546/224; 548/517; 548/518; 548/523; 548/526; 548/557
(58) Field of Search ............... 544/141; 546/208; 548/557; 514/235.5

(56) References Cited

U.S. PATENT DOCUMENTS 5,210,090 A   5/1993   Desai et al.

*Primary Examiner*—Robert W. Ramsuer
(74) *Attorney, Agent, or Firm*—Linda E. Hall; Stephen Venetianer; Charles M. Kinzig

(57) ABSTRACT

The present invention relates to pyrrolyl and pyridyl derivatives, pharmaceutical compositions containing them and their use as inhibitors of urotensin II.

5 Claims, No Drawings

UROTENSIN-II RECEPTOR ANTAGONISTS

This application claims the benefit of Provisional Application No. 60/172,907, filed Dec. 21, 1999.

FIELD OF THE INVENTION

The present invention relates generally to pyrrolyl and pyridyl derivatives, pharmaceutical compositions containing them and their use as urotensin II antagonists.

BACKGROUND OF THE INVENTION

The integrated control of cardiovascular homeostasis is achieved through a combination of both direct neuronal control and systemic neurohormonal activation. Although the resultant release of both contractile and relaxant factors is normally under stringent regulation, an aberration in this status quo can result in cardiohemodynamic dysfunction with pathological consequences.

The principal mammalian vasoactive factors that comprise this neurohumoral axis, namely angiotensin-II, endothelin-1, norepinephrine, all function via an interaction with specific G-protein coupled receptors (GPCR). Urotensin-II, represents a novel member of this neurohumoral axis.

In the fish, this peptide has significant hemodynamic and endocrine actions in diverse end-organ systems and tissues: smooth muscle contraction
  both vascular and non-vascular in origin including smooth muscle preparations from the gastrointestinal tract and genitourinary tract. Both pressor and depressor activity has been described upon systemic administration of exogenous peptide
osmoregulation:
  effects which include the modulation of transepithelial ion ($Na^+$, $Cl^-$) transport. Although a diuretic effect has been described, such an effect is postulated to be secondary to direct renovascular effects (elevated GFR)
metabolism:
  urotensin-II influences prolactin secretion and exhibits a lipolytic effect in fish (activating triacylglycerol lipase resulting in the mobilization of non-esterified free fatty acids)
  (Pearson, et. al. *Proc. Natl. Acad. Sci. (U.S.A.)* 1980, 77, 5021; Conlon, et. al. *J. Exp. Zool.* 1996, 275, 226.)

In studies with human Urotensin-II it was found that it:
was an extremely potent and efficacious vasoconstrictor
exhibited sustained contractile activity that was extremely resistant to wash out
had detrimental effects on cardiac performance (myocardial contractility)

Human Urotensin-II was assessed for contractile activity in the rat-isolated aorta and was shown to be the most potent contractile agonist identified to date. Based on the in vitro pharmacology and in vivo hemodynamic profile of human Urotensin-II it plays a pathological role in cardiovascular diseases characterized by excessive or abnormal vasoconstriction and myocardial dysfunction. (Ames et. al. *Nature* 1999, 401, 282)

Compounds that antagonize the Urotensin-II receptor may be useful in the treatment of congestive heart failure, stroke, ischemic heart disease (angina, myocardial ischemia), cardiac arrhythmia, hypertension (essential and pulmonary), COPD, restenosis, asthma, (Hay DWP, Luttmann Mass., Douglas SA: 2000, Br J Pharmacol: In press.) neurogenic inflammation and metabolic vasculopathies all of which are characterized by abnormal vasoconstriction and/or myocardial dysfunction. Since U-II and GPR14 are both expressed within the mammalian CNS (Ames et. al. *Nature* 1999, 401, 282), they also may be useful in the treatment of addiction, schizophrenia, impulsivity, anxiety, stress, depression, and neuromuscular function. Functional U-II receptors are expressed in rhabdomyosarcomas cell lines and therefore may have oncological indications. Urotensin may also be implicated in various metabolic diseases such as diabetes (Ames et. al. *Nature* 1999, 401, 282, Nothacker et al., *Nature Cell Biology* 1: 383–385, 1999)

SUMMARY OF THE INVENTION

In one aspect this invention provides for pyrrolyl and pyridyl derivatives, and pharmaceutical compositions containing them.

In a second aspect, this invention provides for the use of pyrrolyl and pyridyl derivatives as antagonists of urotensin II.

In another aspect, this invention provides for the use of pyrrolyl and pyridyl derivatives for treating conditions associated with urotensin II imbalance.

In an yet another aspect, this invention provides for the use of these pyrrolyl and pyridyl derivatives for the treatment of congestive heart failure, stroke, ischemic heart disease (angina, myocardial ischemia), cardiac arrhythmia, hypertension (essential and pulmonary), COPD, restenosis, asthma, neurogenic inflammation and metabolic vasculopathies, addiction, schizophrenia, impulsivity, anxiety, stress, depression, neuromuscular function, and diabetes.

The urotensin antagonist may be administered alone or in conjunction with one or more other therapeutic agents, said agents being selected from the group consisting of endothelin receptor antagonists, angiotensin converting enzyme (ACE) inhibitors, vasopeptidase inhibitors, diuretics, digoxin, and dual non-selective β-adrenoceptor and $α_1$-adrenoceptor antagonists.

Other aspects and advantages of the present invention are described further in the following detailed description of the preferred embodiments thereof.

DETAILED DESCRIPTION OF THE INVENTION

The compounds of the invention are represented by structural Formula I:

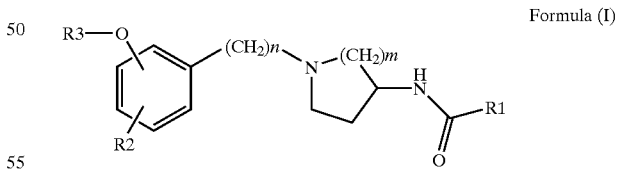

Formula (I)

wherein:
  n is 1 or 2;
  m is 1 or 2;
  R1 is benzofuranyl, naphthyl or phenyl, substituted or unsubstituted with one or two halogen, methyl, trifluoromethyl, methoxy or methylenedioxy groups;
  R2 is hydrogen, one or two halogens, methyl, methoxy, nitro or 2,3-(1,3-butadien-1,4-yl);
  R3 is 3-dimethylaminopropyl, 2-(pyrrolidin-1-yl)ethyl, 2-(1-morpholino)ethyl, 2-(1-piperazinyl)ethyl, (1-methylpyrrolidin-2(S)-yl)methyl, 1-methylpyrrolidin:-3(±)-yl, 1-benzylpiperidin-4-yl, 2(S)-(aminocarbonyl)pyrrolidin-4(S)-yl, pyrrolidin-3(S)-yl, piperidin-4-yl, pyrrolidin-3(R)-yl, or cis-4-aminocyclohexyl;

or a pharmaceutically acceptable salt thereof.

When used herein, the terms 'halogen' and 'halo' include fluorine, chlorine, bromine and iodine and fluoro, chloro, bromo and iodo, respectively.

The compounds of the present invention may contain one or more asymmetric carbon atoms and may exist in racemic or optically active form. All of these compounds and their diastereoisomers are contemplated to be within the scope of the present invention.

$R_1$ is preferably phenyl substituted with one or two halogen, or methyl groups.

$R_2$ preferably is hydrogen, halogen, or methoxy.

$R_3$ preferably is, 2-(1-piperazinyl)ethyl, pyrrolidin-3(S)-yl, piperidin-4-yl, pyrrolidin-3(R)-yl, 1-methylpyrrolidin-3(±)-yl, or 3-dimethylaminopropyl.

Preferred Compounds are:

3,4-Dichloro-N-{(S)-1-[4-(3-dimethylamino-propoxy)-benzyl]-pyrrolidin-3-yl}-benzamide;
3,4-Dichloro-N-{(R)-1-[4-(3-dimethylamino-propoxy)-benzyl]-pyrrolidin-3-yl}-benzamide;
3,4-Dichloro-N-{1-[4-(3dimethylamino-propoxy)-benzyl]-piperidin-4-}-benzamide;
3,4-Dichloro-N-{(S)-1-[4-iodo-3-(2-piperazin-1-yl-ethoxy)-benzyl]-pyrrolidin-3-yl}-benzamide;
N-{(S)-1-[3-Bromo-4-(1-methyl-pyrrolidin-3-yloxy)-benzyl]-pyrrolidin-3-yl}-3,4-dichloro-benzamide;
4-Bromo-N-{(S)-1-[4-(3-dimethylamino-propoxy)-benzyl]-pyrrolidin-3-yl}-benzamide;
4-Bromo-N-{(R)-1-[4-(3-dimethylamino-propoxy)-benzyl]-pyrrolidin-3-yl}-benzamide;
3,4-Dichloro-N-{(S)-1-[3-(3-dimethylamino-propoxy)-4-iodo-benzyl]-pyrrolidin-3-yl}-benzamide;
3,4-Dichloro-N-{(S)-1-[3-chloro-4-(1-methyl-pyrrolidin-3-yloxy)-benzyl]-pyrrolidin-3-yl}-benzamide
3,4-Dichloro-N-{(S)-1-[2-methoxy-4-(2-piperazin-1-yl-ethoxy)-benzyl]-pyrrolidin-3-yl}-benzamide;
N-{(S)-1-[3-Bromo-4-(piperidin-4-yloxy)-benzyl]-pyrrolidin-3-yl}-3,4-dichloro-benzamide;
N-{(S)-1-[3-Bromo-4-((R)-pyrrolidin-3-yloxy)-benzyl]-pyrrolidin-3-yl}-3,4-dichloro-benzamide;
N-{(S)-1-[3-chloro-4-(piperidin-4-yloxy)-benzyl]-pyrrolidin-3-yl}3,4-dichloro-benzamide;
3,4-Dichloro-N-((S)-1-{2-[4-(piperidin-4-yloxy)-3-chlorophenyl]ethyl}-pyrrolidin-3-yl)-benzamide.
3,4-Dichloro-N-((S)-1-{2-[4-(piperidin-4-yloxy)-3-bromophenyl]-ethyl}-pyrrolidin-3-yl)-benzamide.
3,4-Dichloro-N-((S)-1-{2-[3-(piperidin-4-yloxy)-phenyl]-ethyl}-pyrrolidin-3-yl)-benzamide.
3,4-Dichloro-N-((S)-1-{2-[3-(piperidin-4-yloxy)-4-methoxyphenyl]-ethyl}-pyrrolidin-3-yl)-benzamide.
3,4-Dichloro-N-((S)-1-{2-[4-(pyrrolidin-3(S)-yloxy)-3-bromophenyl]-ethyl}-pyrrolidin-3-yl)-benzamide.
3,4-Dichloro-N-((S)-1-{2-[3-(trans4-aminocyclohexyl)-4-methoxyphenyl]-ethyl}-pyrrolidin-3-yl)-benzamide.
3,4-Dichloro-N-((S)-1-{2-[4-(pyrrolidin-3(R)-yloxy)-3-bromophenyl]-ethyl}-pyrrolidin-3-yl)-benzamide.
3,4-Dichloro-N-((S)-1-{2-[4-(pyrrolidin-3(R)-yloxy)-3-nitrophenyl]-ethyl}-pyrrolidin-3-yl)-benzamide.
3,4-Dichloro-N-((S)-1-{2-[3-(pyrrolidin-3(R)-yloxy)-4-methoxyphenyl]-ethyl}-pyrrolidin-3-yl)-benzamide; or
3,4-Dichloro-N-((S)-1-{2-[4-(pyrrolidin-3(R)-yloxy)-3-chlorophenyl]-ethyl}-pyrrolidin-3-yl)-benzamide.

Compounds of Formula (I) may be prepared as outlined in the following scheme:

Scheme 1:

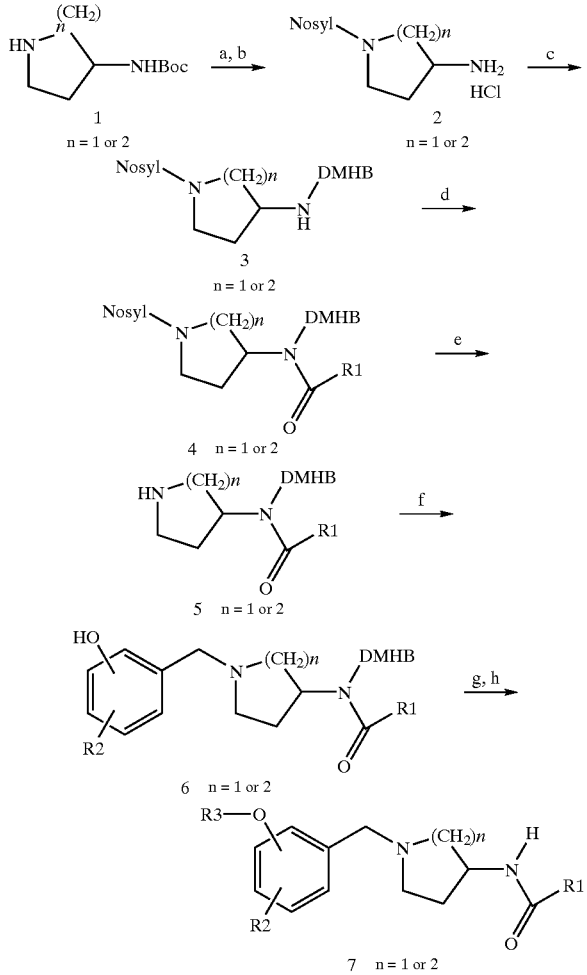

Conditions: a) 2-nitrobenzenesulfonyl chloride, pyridine, $CH_2Cl_2$, 0° C.–rt; b) 4 M HCl in 1,4-dioxane, MeOH, rt; c) 2,6-dimethoxy-4-polystyrenebenzyloxy-benzaldehyde (DMHB resin), $Na(OAc)_3BH$, diisopropylethylamine, 1% acetic acid in 1-methyl-2-pyrrolidinone, rt; d) $R_1COOH$, 1,3-diisopropylcarbodiimide, 1-hydroxy-7-azabenzotriazole, 1-methyl-2-pyrrolidinone, rt; e) $K_2CO_3$, PhSH, 1-methyl-2-pyrrolidinone, rt; f) (R2)(O,H)PhCHO, $Na(OAc)_3BH$, 10% acetic acid in 1-methyl-2-pyrrolidinone, rt; g) $R_3OH$, diisopropyl azodicarboxylate, $PPh_3$, tetrahydrofuran, −78° C.–rt; h) 50% trifluoroacetic acid in 1,2-dichloroethane, rt.

As shown in scheme 1,3(S)-(−)-(tert-butoxycarbonyl-amino)pyrrolidine, 3(R)-(−)-(tert-butoxycarbonyl-amino) pyrrolidine or 4-(tert-butoxycarbonyl-amino)pyrrolidine (1) was converted to amine HCl salt 2 which was reacted with 2,6-dimethoxy-4-polystyrenebenzyloxy-benzaldehyde (DMHB resin) to afford Resin-bound amine 3. Reactions of resin-bound amine 3 with various acids provided resin-bound amides 4 which were subsequently treated with potassium carbonate and thiophenol to give secondary amines 5. Reactions of resin-bound amines 5 with various hydroxy benzaldehydes produced resin-bound phenols 6. Phenols 6 were then reacted with various alcohols in the presence of triphenylphosphine and diisopropyl azodicarboxylate to give the corresponding resin-bound phenol ethers which were treated with 50% trifluoroacetic acid in 1,2-dichloroethane to afford targetted compounds 7.

Compounds of Formula (I) may be made by the process outlined in Scheme 2.

(DMHB resin), Na(Oac)$_3$BH, diisopropylethylamine, 1% acetic acid in 1-methyl-2-pyrrolidinone, rt; d) R$_1$COOH, 1,3-diisopropylcarbodiimide, 1-hydroxy-7-azabenzotriazole, 1-methyl-2-pyrrolidinone, rt; e) K$_2$CO$_3$, PhSH, 1-methyl-2-pyrrolidinone, rt; f) bis-nosylates 8, tetrabutylammonium iodide, 1-methyl-2-pyrrolidinone, rt to

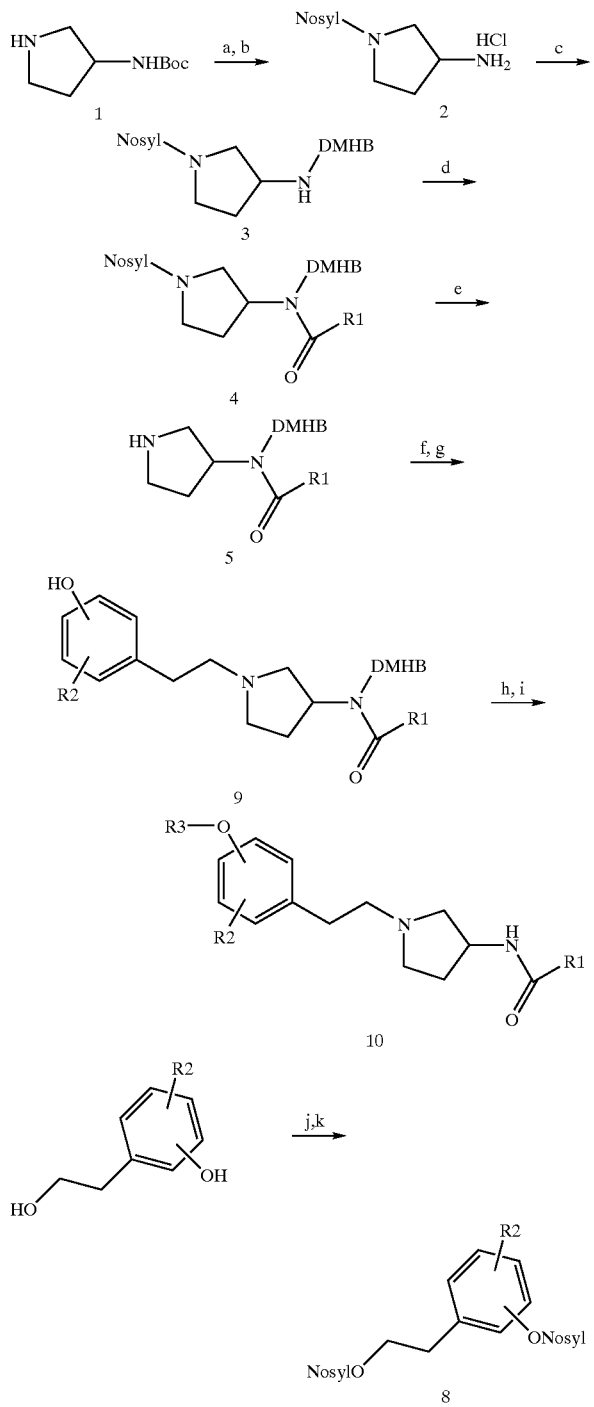

Conditions: a) 2-nitrobenzenesulfonyl chloride, pyridine, CH$_2$Cl$_2$, 0° C.–rt; b) 4 M HCl in 1,4-dioxane, MeOH, rt; c) 2,6-dimethoxy-4-polystyrenebenzyloxy-benzaldehyde 65° C.; g) potassium trimethylsilanolate, tetrahydrofuran, rt; h) R$_3$OH, diisopropyl azodicarboxylate, PPh$_3$, tetrahydrofuran, –78° C.–rt; i) 50% trifluoroacetic acid in 1,2-dichloroethane, rt; j) 2-nitrobenzenesulfonyl chloride, sodium hydride, tetrahydrofuran, rt; k) ether, water, 0° C.

As shown in scheme 2,3(S)-(-)-(tert-butoxycarbonylamino)pyrrolidine (1) was converted to amine HCl salt 2 which was reacted with 2,6-dimethoxy-4-polystyrenebenzyloxy-benzaldehyde (DMHB resin) to afford resin-bound amine 3 (Scheme 1). Reactions of resin-bound amine 3 with various acids provided resin-bound amides 4 which were subsequently treated with potassium carbonate and thiophenol to give secondary amines 5. Bis-nosylates 8 were synthesized from various commercially available or known hydroxyphenethyl alcohols. Phenols 9 were prepared by reactions of secondary amines 5 with bis-nosylates 8 in the presence of tetrabutylammonium iodide, followed by hydrolysis of the resulting mononosylate intermediates. Phenols 9 were then reacted with various alcohols in the presence of triphenylphosphine and diisopropyl azodicarboxylate to give the corresponding resin-bound phenol ethers which were treated with 50% trifluoroacetic acid in 1,2-dichloroethane to afford targetted compounds 10.

In order to use a compound of the Formula (I) or a pharmaceutically acceptable salt thereof for the treatment of humans and other mammals it is normally formulated in accordance with standard pharmaceutical practice as a pharmaceutical composition.

Compounds of Formula (I) and their pharmaceutically acceptable salts may be administered in a standard manner for the treatment of the indicated diseases, for example orally, parenterally, sub-lingually, transdermally, rectally, via inhalation or via buccal administration.

Compounds of Formula (I) and their pharmaceutically acceptable salts which are active when given orally can be formulated as syrups, tablets, capsules and lozenges. A syrup formulation will generally consist of a suspension or solution of the compound or salt in a liquid carrier for example, ethanol, peanut oil, olive oil, glycerine or water with a flavoring or coloring agent. Where the composition is in the form of a tablet, any pharmaceutical carrier routinely used for preparing solid formulations may be used. Examples of such carriers include magnesium stearate, terra alba, talc, gelatin, agar, pectin, acacia, stearic acid, starch, lactose and sucrose. Where the composition is in the form of a capsule, any routine encapsulation is suitable, for example using the aforementioned carriers in a hard gelatin capsule shell. Where the composition is in the form of a soft gelatin shell capsule any pharmaceutical carrier routinely used for preparing dispersions or suspensions may be considered, for example aqueous gums, celluloses, silicates or oils and are incorporated in a soft gelatin capsule shell.

Typical parenteral compositions consist of a solution or suspension of the compound or salt in a sterile aqueous or non-aqueous carrier optionally containing a parenterally acceptable oil, for example polyethylene glycol, polyvinylpyrrolidone, lecithin, arachis oil, or sesame oil.

Typical compositions for inhalation are in the form of a solution, suspension or emulsion that may be administered as a dry powder or in the form of an aerosol using a conventional propellant such as dichlorodifluoromethane or trichlorofluoromethane.

A typical suppository formulation comprises a compound of Formula (1) or a pharmaceutically acceptable salt thereof which is active when administered in this way, with a binding and/or lubricating agent, for example polymeric glycols, gelatins, cocoa-butter or other low melting vegetable waxes or fats or their synthetic analogues.

Typical transdermal formulations comprise a conventional aqueous or non-aqueous vehicle, for example a cream, ointment, lotion or paste or are in the form of a medicated plaster, patch or membrane.

Preferably the composition is in unit dosage form, for example a tablet, capsule or metered aerosol dose, so that the patient may administer to themselves a single dose.

Each dosage unit for oral administration contains suitably from 0.1 mg to 500 mg/Kg, and preferably from 1 mg to 100 mg/Kg, and each dosage unit for parenteral administration contains suitably from 0.1 mg to 100 mg, of a compound of Formula (I) or a pharmaceutically acceptable salt thereof calculated as the free acid. Each dosage unit for intranasal administration contains suitably 1–400 mg and preferably 10 to 200 mg per person. A topical formulation contains suitably 0.01 to 1.0% of a compound of Formula (I).

The daily dosage regimen for oral administration is suitably about 0.01 mg/Kg to 40 mg/Kg, of a compound of Formula (I) or a pharmaceutically acceptable salt thereof calculated as the free acid. The daily dosage regimen for parenteral administration is suitably about 0.001 mg/Kg to 40 mg/Kg, of a compound of the Formula (I) or a pharmaceutically acceptable salt thereof calculated as the free acid. The daily dosage regimen for intranasal administration and oral inhalation is suitably about 10 to about 500 mg/person. The active ingredient may be administered from 1 to 6 times a day, sufficient to exhibit the desired activity.

These pyrrolidine analogs may be used for the treatment of congestive heart failure, stroke, ischemic heart disease (angina, myocardial ischemia), cardiac arrhythmia, hypertension (essential and pulmonary), COPD, restenosis, asthma, neurogenic inflammation and metabolic vasculopathies, addiction, schizophrenia, impulsivity, anxiety, stress, depression, neuromuscular function, and diabetes.

The urotensin antagonist may be administered alone or in conjunction with one or more other therapeutic agents, said agents being selected from the group consisting of endothelin receptor antagonists, angiotensin converting enzyme (ACE) inhibitors, vasopeptidase inhibitors, diuretics, digoxin, and dual non-selective β-adrenoceptor and $α_1$-adrenoceptor antagonists.

No unacceptable toxicological effects are expected when compounds of the invention are administered in accordance with the present invention.

The biological activity of the compounds of Formula (I) are demonstrated by the following tests:

Radioligand Binding

HEK-293 cell membranes containing stable cloned human and rat GPR-14 (20 ug/assay) were incubated with 200 pM [125I] h-U-II (200 Ci/mmol$^{-1}$ in the presence of increasing concentrations of test compounds in DMSO (0.1 nM to 10 uM), in a final incubation volume of 200 ul (20 mM Tris-HCl, 5 mM MgCl2). Incubation was done for 30 minutes at room temperature followed by filtration GF/B filters with Brandel cell harvester. $^{125}$I labeled U-II binding was quantitated by gamma counting. Nonspecific binding was defined by $^{125}$I U-II binding in the presence of 100 nM of unlabeled human U-II. Analysis of the data was performed by nonlinear least square fitting.

$Ca^{2+}$-mobilization

A microtitre plate based $Ca^{2+}$-mobilization FLIPR assay (Molecular Devices, Sunnyvale, Calif.) was used for the functional identification of the ligand activating HEK-293 cells expressing (stable) recombinant GPR-14. The day following transfection, cells were plated in a poly-D-lysine coated 96 well black/clear plates. After 18–24 hours the media was aspirated and Fluo 3AM-loaded cells were exposed to various concentrations (10 nM to 30 uM) of test compounds followed by h-U-II. After initiation of the assay, fluorescence was read every second for one minute and then every 3 seconds for the following one minute. The inhibitory concentration at 50% (IC50) was calculated for various test compounds.

Inositol Phosphates Assays

HEK-293-GPR14 cells in T150 flask were prelabeled overnight with 1 uCi myo-[$^3$H] inositol per ml of inositol free Dulbecco's modified Eagel's medium. After labeling, the cells were washed twice with Dulbecco's phosphate-buffered saline (DPBS) and then incubated in DPBS containing 10 mM LiCl for 10 min at 37° C. The experiment was initiated by the addition of increasing concentrations of h-U-II (1 pM to 1 μM) in the absence and presence of three different concentrations (0.3, 1 and 10 uM) of test compounds and the incubation continued for an additional 5 min at 37° C. after which the reaction was terminated by the addition of 10% (final concentration) trichloroacetic acid and centrifugation. The supernatants were neutralized with 100 ul of 1M Trizma base and the inositol phosphates were separated on AG 1-X8 columns (0.8 ml packed, 100–200 mesh) in formate phase. Inositol monophosphate was eluted with 8 ml of 200 mM ammonium formate. Combined inositol di and tris phosphate was eluted with 4 ml of 1M ammonium formate/0.1 M formic acid. Eluted fractions were counted in beta scintillation counter. Based on shift from the control curve KB was calculated.

Activity for the compounds of this invention range from (radioligand binding assay): Ki=1 nM–10000 nM (example 13 Ki=360 nM)

EXAMPLE 1

Preparation of 3(S)-(3,4-dichlorobenzoylamino)-1-[4-(3-dimethylaminopropoxy)benzyl]pyrrolidine a) 3(S)-amino-N-(2-nitrobenzenesulfonyl)pyrrolidine HCl Salt To a solution of 3(S)-(−)-(tert-butoxycarbonyl-amino)pyrrolidine (20.12 g, 108 mmol) in 250 mL of anhydrous methylene chloride at 0° C. was added 13.1 mL (162 mmol) of anhydrous pyridine, followed by slow addition of 25.2 g (113.4 mmol) of 2-nitrobenzenesulfonyl chloride. The mixture was warmed to rt over 1 h and was stirred at rt for 16 h. The mixture was poured into 300 mL of 1 M aqueous NaHCO$_3$ solution. After the resulting mixture was stirred at rt for 30 min, the organic layer was separated and was washed with 500 mL of 1N aqueous HCl solution twice. The resulting organic layer was dried over MgSO$_4$ and concentrated in vacuo. The residue was used for the the next step without further purification.

To a mixture of the above residue in 140 mL of anhydrous MeOH was added 136 mL (544 mmol) of 4 M HCl in 1,4-dioxane solution. The mixture was stirred at rt for 16 h, concentrated in vacuo and further dried in vaccum oven at 35° C. for 24 h to yield 3(S)-amino-N-(2-nitrobenzenesulfonyl)pyrrolidine HCl salt as a yellow solid (30.5 g, 92% over the two steps): $^1$H NMR (400 MHz, d$_6$-DMSO) δ8.63 (s, 3 H), 8.08–7.98 (m, 2 H), 7.96–7.83 (m, 2 H), 3.88–3.77 (m, 1 H), 3.66–3.56 (m, 2 H), 3.46–3.35 (m, 2 H), 2.28–2.16 (m, 1 H), 2.07–1.96 (m, 1 H).

b) 3(S)-(3,4-dichlorobenzoylamino)-1-[4-(3-dimethylaminopropoxy)benzyl]pyrrolidine To a mixture of 15.0 g (21.6 mmol, 1.44 mmol/g) of 2,6-dimethoxy-4-polystyrenebenzyloxy-benzaldehyde (DMHB resin) in 326 mL of 1% acetic acid in anhydrous 1-methyl-2-pyrrolidinone was added 20.0 g (65.1 mmol) of example 1a and 18.9 mL (108.5 mmol) of diisopropylethyl amine, followed by addition of 23.0 g (108.5 mmol) of sodium triacetoxyborohydride. After the resulting mixture was shaken at rt for 72 h, the resin was washed with DMF (3×500 mL), CH$_2$Cl$_2$/MeOH (1:1, 3×500 mL) and MeOH (3×500 mL). The resulting resin was dried in vacuum oven at 35° C. for 24 h. Elemental analysis N: 4.16, S: 3.12.

To a mixture of 10.0 g (10.75 mmol, 1.075 mmol/g) of the above resin in 164 mL of anhydrous 1-methyl-2-pyrrolidinone was added 9.42 g (49.3 mmol) of 3,4-dichlorobenzoic acid and 1.34 g (9.86 mmol) of 1-hydroxy-7-azabenzotriazole, followed by addition of 9.26 mL (59.2 mmol) of 1,3-diisopropylcarbodiimide. After the resulting mixture was shaken at rt for 24 h, the resin was washed with DMF (3×250 mL), CH$_2$Cl$_2$/MeOH (1:1, 3×250 mL) and MeOH (3×250 mL). The resulting resin was dried in vacuum oven at 35° C. for 24 h. An analytical amount of resin was cleaved with 50% trifluoroacetic acid in dichloroethane for 2 h at rt. The resulting solution was concentrated in vacuo: MS (ESI) 444 [M+H]$^+$.

To a mixture of the above dry resin (10.75 mmol) in 329 mL of 1-methyl-2-pyrrolidinone was added 13.7 g (98.6 mmol) of K$_2$CO$_3$ and 5.06 mL (49.3 mmol) of PhSH. After the resulting mixture was shaken at rt for 4 h, the resin was washed with DMF (3×500 mL), H$_2$O (3×500 mL), DMF (3×500 mL), CH$_2$Cl$_2$/MeOH (1:1, 3×500 mL) and MeOH (3×500 mL). The resulting resin was dried in vacuum oven at 35° C. for 24 h. An analytical amount of resin was cleaved with 50% trifluoroacetic acid in dichloroethane for 2 h at rt. The resulting solution was concentrated in vacuo: MS (ESI) 517 [2M+H]$^+$, 259 [M+H]$^+$.

To a mixture of 300 mg (0.320 mmol, 1.066 mmol/g) of the above dry resin in 10.7 mL of 10% HOAc in anhydrous 1-methyl-2-pyrrolidinone solution was added 390 mg (3.20 mmol) of 4-hydroxybenzaldehyde and 679 mg (3.20 mmol) of sodium triacetoxyborohydride. After the resulting mixture was shaken at rt for 72 h, the resin was washed with DMF (3×15 mL), CH$_2$Cl$_2$/MeOH (1:1, 3×15 mL) and MeOH (3×15 mL). The resulting resin was dried in vacuum oven at 35° C. for 24 h. An analytical amount of resin was cleaved with 50% trifluoroacetic acid in dichloroethane for 2 h at rt. The resulting solution was concentrated in vacuo: MS (ESI) 365 [M+H]$^+$.

To a mixture of the above dry resin (0.320 mmol) in 17.7 mL of anhydrous THF was added 379 μL (3.20 mmol) of 3-dimethylaminopropanol and 839 mg (3.20 mmol) of triphenylphosphine. After the mixture was cooled to −78° C., 630 μL (3.20 mmol) of diisopropyl azodicarboxylate was added to the cold mixture. The resulting mixture was kept at −70° C. for 30 min while shaking. The mixture was then allowed to warm to 0° C. over 1 h and shaken at rt for 16 h. The resin was washed with DMF (3×25 mL), CH$_2$Cl$_2$/MeOH (1:1, 3×25 mL) and MeOH (3×25 mL). The resulting resin was dried in vacuum oven at 35° C. for 24 h. The dry resin was treated with 4 mL of 50% trifluoroacetic acid in dichloroethane at rt for 2 h. After the cleavage solution was collected, the resin was treated with another 4 mL of 50% trifluoroacetic acid in dichloroethane at rt for 10 min. The combined cleavage solutions were concentrated in vacuo. The residue was purified using a Gilson semi-preparative HPLC system with a YMC ODS-A (C-18) column 50 mm by 20 mm ID, eluting with 10% B to 90% B in 3.2 min, hold for 1 min where A=H$_2$O (0.1% trifluoroacetic acid) and B=CH$_3$CN (0.1% trifluoroacetic acid) pumped at 25 mL/min, to produce 3(S)-(3,4-dichlorobenzoylamino)-1-[4-(3-dimethylaminopropoxy)benzyl]pyrrolidine as a bis-trifluoroacetic acid salt (clear oil, 150 mg, 69% over 5 steps): MS (ESI) 450 [M+H]$^+$.

Compounds derived from Scheme 1:

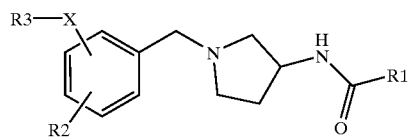

| Example | R1 | X | R2 | R3 | MS (ES+) m/e |
|---|---|---|---|---|---|
| 2 | phenyl | 4-oxy | H | 3-dimethylaminopropyl | 382 (M + H) |
| 3 | 4-bromophenyl | 4-oxy | H | 3-dimethylaminopropyl | 460 (M + H) |
| 4 | 3,4-methylene dioxyphenyl | 4-oxy | H | 3-dimethylaminopropyl | 426 (M + H) |
| 5 | benzofuran-2-yl | 4-oxy | H | 3-dimethylaminopropyl | 422 (M + H) |
| 6 | 3,4-dichlorophenyl | 3-oxy | 4-iodo | 3-dimethylaminopropyl | 576 (M + H) |
| 7 | 3,4-dichlorophenyl | 4-oxy | 2,3-(1,3-butadien-1,4-yl) | 3-dimethylaminopropyl | 500 (M + H) |
| 8 | 3,4-dichlorophenyl | 4-oxy | 2-methoxy | 3-dimethylaminopropyl | 480 (M + H) |
| 9 | 3,4-dichlorophenyl | 4-oxy | 3-chloro | 3-dimethylaminopropyl | 484 (M + H) |
| 10 | 3,4-dichlorophenyl | 4-oxy | 3-methyl | 3-dimethylaminopropyl | 464 (M + H) |
| 11 | 3,4-dichlorophenyl | 4-oxy | 3-bromo | 3-dimethylaminopropyl | 528 (M + H) |
| 12 | 3,4-dichlorophenyl | 3-oxy | 4-iodo | 2-(pyrrolidin-1-yl)ethyl | 588 (M + H) |
| 13 | 3,4-dichlorophenyl | 4-oxy | 2,3-(1,3-butadien-1,4-yl) | 2-(pyrrolidin-1-yl)ethyl | 512 (M + H) |
| 14 | 3,4-dichlorophenyl | 4-oxy | 2-methoxy | 2-(pyrrolidin-1-yl)ethyl | 492 (M + H) |
| 15 | 3,4-dichlorophenyl | 4-oxy | 3-chloro | 2-(pyrrolidin-1-yl)ethyl | 496 (M + H) |
| 16 | 3,4-dichlorophenyl | 4-oxy | 3-methyl | 2-(pyrrolidin-1-yl)ethyl | 476 (M + H) |
| 17 | 3,4-dichlorophenyl | 4-oxy | 3-bromo | 2-(pyrrolidin-1-yl)ethyl | 540 (M + H) |
| 18 | 3,4-dichlorophenyl | 3-oxy | H | 2-(1-morpholino)ethyl | 478 (M + H) |
| 19 | 3,4-dichlorophenyl | 3-oxy | H | 2-(1-piperazinyl)ethyl | 477 (M + H) |
| 20 | 3,4-dichlorophenyl | 3-oxy | 4-iodo | 2-(1-piperazinyl)ethyl | 603 (M + H) |
| 21 | 3,4-dichlorophenyl | 4-oxy | 2,3-(1,3-butadien-1,4-yl) | 2-(1-piperazinyl)ethyl | 527 (M + H) |
| 22 | 3,4-dichlorophenyl | 4-oxy | 2-methoxy | 2-(1-piperazinyl)ethyl | 507 (M + H) |
| 23 | 3,4-dichlorophenyl | 4-oxy | 3-chloro | 2-(1-piperazinyl)ethyl | 511 (M + H) |
| 24 | 3,4-dichlorophenyl | 4-oxy | 3-methyl | 2-(1-piperazinyl)ethyl | 491 (M + H) |
| 25 | 3,4-dichlorophenyl | 4-oxy | 3-bromo | 2-(1-piperazinyl)ethyl | 555 (M + H) |
| 26 | 3,4-dichlorophenyl | 4-oxy | H | (1-methylpyrrolidin-2(S)-yl)methyl | 462 (M + H) |
| 27 | 3,4-dichlorophenyl | 3-oxy | H | (1-methylpyrrolidin-2(S)-yl)methyl | 462 (M + H) |
| 28 | 3,4-dichlorophenyl | 3-oxy | 4-iodo | (1-methylpyrrolidin-2(S)-yl)methyl | 588 (M + H) |
| 29 | 3,4-dichlorophenyl | 4-oxy | 3-chloro | (1-methylpyrrolidin-2(S)-yl)methyl | 496 (M + H) |
| 30 | 3,4-dichlorophenyl | 4-oxy | 3-bromo | (1-methylpyrrolidin-2(S)-yl)methyl | 540 (M + H) |
| 31 | 3,4-dichlorophenyl | 4-oxy | H | 1-methylpyrrolidin-3(±)-yl | 448 (M + H) |
| 32 | 3,4-dichlorophenyl | 3-oxy | H | 1-methylpyrrolidin-3(±)-yl | 448 (M + H) |
| 33 | 3,4-dichlorophenyl | 3-oxy | 4-iodo | 1-methylpyrrolidin-3(±)-yl | 574 (M + H) |
| 34 | 3,4-dichlorophenyl | 4-oxy | 2,3-(1,3-butadien-1,4-yl) | 1-methylpyrrolidin-3(±)-yl | 498 (M + H) |
| 35 | 3,4-dichlorophenyl | 4-oxy | 3-chloro | 1-methylpyrrolidin-3(±)-yl | 482 (M + H) |
| 36 | 3,4-dichlorophenyl | 4-oxy | 3-methyl | 1-methylpyrrolidin-3(±)-yl | 462 (M + H) |
| 37 | 3,4-dichlorophenyl | 4-oxy | 3-bromo | 1-methylpyrrolidin-3(±)-yl | 526 (M + H) |
| 38 | 3,4-dichlorophenyl | 4-oxy | 2,3-(1,3-butadien-1,4-yl) | 1-benzylpiperidin-4-yl | 588 (M + H) |
| 39 | 3,4-dichlorophenyl | 4-oxy | 2-methoxy | 1-benzylpiperidin-4-yl | 568 (M + H) |
| 40 | 3,4-dichlorophenyl | 4-oxy | 3-chloro | 1-benzylpiperidin-4-yl | 572 (M + H) |
| 41 | 3,4-dichlorophenyl | 4-oxy | 3-methyl | 1-benzylpiperidin-4-yl | 552 (M + H) |
| 42 | 3,4-dichlorophenyl | 4-oxy | 3-bromo | 1-benzylpiperidin-4-yl | 616 (M + H) |
| 43 | 3,4-dichlorophenyl | 4-oxy | H | 2(S)-(aminocarbonyl)pyrrolidin-4(S)-yl | 477 (M + H) |
| 44 | 3,4-dichlorophenyl | 4-oxy | 2-methoxy | 2(S)-(aminocarbonyl)pyrrolidin-4(S)-yl | 507 (M + H) |
| 45 | 3,5-dichlorophenyl | 4-oxy | H | 3-dimethylaminopropyl | 450 (M + H) |
| 46 | 4-chloro-3-methyl phenyl | 4-oxy | H | 3-dimethylaminopropyl | 430 (M + H) |
| 47 | 4-bromo-3-methyl phenyl | 4-oxy | H | 3-dimethylaminopropyl | 474 (M + H) |
| 48 | 3,4-dichlorophenyl | 4-oxy | 3-bromo | piperidin-4-yl | 526 (M + H) |
| 49 | 3,4-dichlorophenyl | 4-oxy | 3-bromo | pyrrolidin-3(R)-yl | 512 (M + H) |
| 50 | 3,4-dichlorophenyl | 4-oxy | 3-chloro | piperidin-4-yl | 482 (M + H) |
| 51 | 3,4-dichlorophenyl | 4-oxy | 3-bromo | pyrrolidin-3(S)-yl | 512 (M + H) |
| 52 | 3,4-dichlorophenyl | 4-oxy | 3,5-dichloro | piperidin-4-yl | 516 (M + H) |
| 53 | 3,4-dichlorophenyl | 4-oxy | 3-chloro | pyrrolidin-3(S)-yl | 468 (M + H) |
| 54 | 3,4-dichlorophenyl | 4-oxy | 3,5-dichloro | pyrrolidin-3(S)-yl | 502 (M + H) |

Compounds derived from Scheme 1:

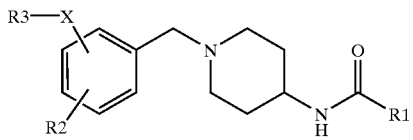

| Example | R1 | X | R2 | R3 | MS (ES+) m/e |
|---|---|---|---|---|---|
| 55 | 3,4-dichlorophenyl | 4-oxy | H | 3-dimethylaminopropyl | 464 (M + H) |
| 56 | 3,5-dichlorophenyl | 4-oxy | H | 3-dimethylaminopropyl | 464 (M + H) |
| 57 | 2,4-dichlorophenyl | 4-oxy | H | 3-dimethylaminopropyl | 464 (M + H) |
| 58 | 4-chloro-3-methyl phenyl | 4-oxy | H | 3-dimethylaminopropyl | 444 (M + H) |
| 59 | 4-bromo-3-methyl phenyl | 4-oxy | H | 3-dimethylaminopropyl | 488 (M + H) |
| 60 | 4-trifluoromethyl phenyl | 4-oxy | H | 3-dimethylaminopropyl | 464 (M + H) |
| 61 | 2-naphthyl | 4-oxy | H | 3-dimethylaminopropyl | 446 (M + H) |

EXAMPLE 62

Preparation of 3,4-dichloro-N-((S)-1-{2-[4-((S)-pyrrolidin-3-yloxy)-phenyl]-ethyl}-pyrrolidin-3-yl)-benzamide a) 3(S)-amino-N-(2-nitrobenzenesulfonyl) pyrrolidine HCl salt To a solution of 3(S)-(−)-(tert-butoxycarbonyl-amino) pyrrolidine (20.12 g, 108 mmol) in 250 mL of anhydrous methylene chloride at 0° C. was added 13.1 mL (162 mmol) of anhydrous pyridine, followed by slow addition of 25.2 g (113.4 mmol) of 2-nitrobenzenesulfonyl chloride. The mixture was warmed to rt over 1 h and was stirred at rt for 16 h. The mixture was poured into 300 mL of 1 M aqueous $NaHCO_3$ solution. After the resulting mixture was stirred at rt for 30 min, the organic layer was separated and was washed with 500 mL of 1 N aqueous HCl solution twice. The resulting organic layer was dried over $MgSO_4$ and concentrated in vacuo. The residue was used for the next step without further purification.

To a mixture of the above residue in 140 mL of anhydrous MeOH was added 136 mL (544 mmol) of 4 M HCl in 1,4-dioxane solution. The mixture was stirred at rt for 16 h, concentrated in vacuo and further dried in vaccum oven at 35° C. for 24 h to yield 3(S)-amino-N-(2-nitrobenzenesulfonyl)pyrrolidine HCl salt as a yellow solid (30.5 g, 92% over the two steps): $^1$H NMR (400 MHz, $d_6$-DMSO) $\delta$8.63 (s, 3 H), 8.08–7.98 (m, 2 H), 7.96–7.83 (m, 2 H), 3.88–3.77 (m, 1 H), 3.66–3.56 (m, 2 H), 3.46–3.35 (m, 2 H), 2.28–2.16 (m, 1 H), 2.07–1.96 (m, 1 H).

b) 2-nitrobenzenesulfonic acid 2-[4-(2-nitrobenzenesulfonyloxy)-phenyl]-ethyl ester To a mixture of 2.76 g (20 mmol) of 4-hydroxyphenethyl alcohol in 70 mL of anhydrous tetrahydrofuran at rt was added 4.8 g (200 mmol) of sodium hydride (95%, dry powder). After stirring at rt for 10 min, 18.5 g (80 mmol) of 2-nitrobenzenesulfonyl chloride was added. After the resulting mixture was stirred at rt for 16 h, 250 mL of ether was added. The mixture was cooled to 0° C. and water was slowly added to the the mixture to quench excess sodium hydride. After quenching process was completed, additional 300 mL of water was added. The resulting precipitate was collected via filtration, washed with water and dried in vacuo to yield 2-nitrobenzenesulfonic acid 2-[4-(2-nitrobenzenesulfonyloxy)-phenyl]-ethyl ester as a white powder (9.13 g, 90%): MS (ESI) 509 [M+H]$^+$.

c) 3,4-dichloro-N-((S)-1-{2-[4-((S)-pyrrolidin-3-yloxy)-phenyl]-ethyl}-pyrrolidin-3-yl)-benzamide To a mixture of 15.0 g (21.6 mmol, 1.44 mmol/g) of 2,6-dimethoxy-4-polystyrenebenzyloxy-benzaldehyde (DMHB resin) in 326 mL of 1% acetic acid in anhydrous 1-methyl-2-pyrrolidinone was added 20.0 g (65.1 mmol) of example 1a and 18.9 mL (108.5 mmol) of diisopropylethyl amine, followed by addition of 23.0 g (108.5 mmol) of sodium triacetoxyborohydride. After the resulting mixture was shaken at rt for 72 h, the resin was washed with DMF (3×500 mL), $CH_2Cl_2$/MeOH (1:1, 3×500 mL) and MeOH (3×500 mL). The resulting resin was dried in vacuum oven at 35° C. for 24 h. Elemental analysis N: 4.16, S: 3.12.

To a mixture of 10.0 g (10.75 mmol, 1.075 mmol/g) of the above resin in 164 mL of anhydrous 1-methyl-2-pyrrolidinone was added 9.42 g (49.3 mmol) of 3,4-dichlorobenzoic acid and 1.34 g (9.86 mmol) of 1-hydroxy-7-azabenzotriazole, followed by addition of 9.26 mL (59.2 mmol) of 1,3-diisopropylcarbodiimide. After the resulting mixture was shaken at rt for 24 h, the resin was washed with DMF (3×250 mL), $CH_2Cl_2$/MeOH (1:1, 3×250 mL) and MeOH (3×250 mL). The resulting resin was dried in vacuum oven at 35° C. for 24 h. An analytical amount of resin was cleaved with 50% trifluoroacetic acid in dichloroethane for 2 h at rt. The resulting solution was concentrated in vacuo: MS (ESI) 444 [M+H]$^+$.

To a mixture of the above dry resin (10.75 mmol) in 329 mL of 1-methyl-2-pyrrolidinone was added 13.7 g (98.6 mmol) of $K_2CO_3$ and 5.06 mL (49.3 mmol) of PhSH. After the resulting mixture was shaken at rt for 4 h, the resin was washed with DMF (3×500 mL), $H_2O$ (3×500 mL), DMF (3×500 mL), $CH_2Cl_2$/MeOH (1:1, 3×500 mL) and MeOH (3×500 mL). The resulting resin was dried in vacuum oven at 35° C. for 24 h. An analytical amount of resin was cleaved with 50% trifluoroacetic acid in dichloroethane for 2 h at rt. The resulting solution was concentrated in vacuo: MS (ESI) 517[2M+H]$^+$, 259 [M+H]$^+$.

To a mixture of 200 mg (0.2132 mmol, 1.066 mmol/g) of the above dry resin in 7.1 mL of anhydrous 1-methyl-2-pyrrolidinone solution was added 543 mg (1.066 mmol) of 2-nitrobenzenesulfonic acid 2-[4-(2-nitrobenzenesulfonyloxy)-phenyl]-ethyl ester and 788 mg (2.132 mmol) of tetrabutylammonium iodide. After the resulting mixture was shaken at rt for 8 days and subsequently at 65° C. for 20 h, the resin was washed with DMF (3×10 mL), $CH_2Cl_2$/MeOH (1:1, 3×10 mL) and THF (3×10 mL). The resulting resin was dried in vacuum oven at 35° C.

for 24 h. An analytical amount of resin was cleaved with 50% trifluoroacetic acid in dichloroethane for 2 h at rt. The resulting solution was concentrated in vacuo: MS (ESI)564 [M+H]+.

To a mixture of the above dry resin (0.2132 mmol) in 5 mL of anhydrous tetrahydrofuran was added 274 mg (2.132 mmol) of potassium trimethylsilanolate (90%). After the mixture was shaken at rt for 16 h, the resin was washed with THF (3×10 mL) and $CH_2Cl_2$/MeOH (1:1, 6×10 mL). The resulting resin was dried in vacuum oven at 35° C. for 24 h. An analytical amount of resin was cleaved with 50% trifluoroacetic acid in dichloroethane for 2 h at rt. The resulting solution was concentrated in vacuo: MS (ESI) 379 [M+H]+.

To a mixture of the above dry resin (0.2132 mmol) in 10.7 mL of anhydrous tetrahydrofuran was added 399 mg (2.132 mmol) of (R)-3-hydroxy-pyrrolidine-1-carboxylic acid tert-butyl ester (Kucznierz, et. al. *J. Med. Chem.* 1998, 41, 4983–4994) and 559 mg (2.132 mmol) of triphenylphosphine. After the mixture was cooled to −78° C., 420 μL (2.132 mmol) of diisopropyl azodicarboxylate was added to the cold mixture. The resulting mixture was kept at −70° C. for 30 min while shaking. The mixture was then allowed to warm to 0° C. over 1 h and shaken at rt for 16 h. The resin was washed with DMF (3×10 mL), $CH_2Cl_2$/MeOH (1:1, 3×10 mL) and MeOH (3×10 mL). The resulting resin was dried in vacuum oven at 35° C. for 24 h. The dry resin was treated with 4 mL of 50% trifluoroacetic acid in dichloroethane at rt for 2 h. After the cleavage solution was collected, the resin was treated with another 4 mL of 50% trifluoroacetic acid in dichloroethane at rt for 10 min. The combined cleavage solutions were concentrated in vacuo. The residue was purified using a Gilson semi-preparative HPLC system with a YMC ODS-A (C-18) column 50 mm by 20 mm ID, eluting with 10% B to 90% B in 3.2 min, hold for 1 min where A=$H_2O$ (0.1% trifluoroacetic acid) and B=$CH_3CN$ (0.1% trifluoroacetic acid) pumped at 25 mL/min, to produce 3,4-dichloro-N-((S)-1-{2-[4-((S)-pyrrolidin-3-yloxy)-phenyl]-ethyl}-pyrrolidin-3-yl)-benzamide as a bis-trifluoroacetic acid salt (clear oil, 21 mg, 22% over 6 steps): MS (ESI) 448 [M+H]+.

Compounds derived from Scheme 2:

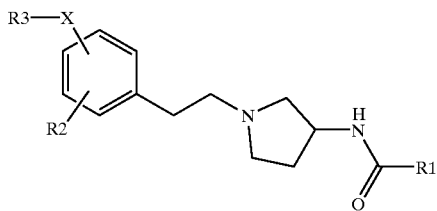

| Example | R1 | X | R2 | R3 | MS (ES+) m/e |
|---|---|---|---|---|---|
| 63 | 3,4-dichlorophenyl | 4-oxy | H | piperidin-4-yl | 462 (M + H) |
| 64 | 3,4-dichlorophenyl | 4-oxy | 3-fluoro | piperidin-4-yl | 480 (M + H) |
| 65 | 3,4-dichlorophenyl | 4-oxy | 3-chloro | piperidin-4-yl | 496 (M + H) |
| 66 | 3,4-dichlorophenyl | 4-oxy | 3-bromo | piperidin-4-yl | 540 (M + H) |
| 67 | 3,4-dichlorophenyl | 4-oxy | 3-methoxy | piperidin-4-yl | 492 (M + H) |
| 68 | 3,4-dichlorophenyl | 4-oxy | 3-nitro | piperidin-4-yl | 507 (M + H) |
| 69 | 3,4-dichlorophenyl | 3-oxy | H | piperidin-4-yl | 462 (M + H) |
| 70 | 3,4-dichlorophenyl | 3-oxy | 4-methoxy | piperidin-4-yl | 492 (M + H) |
| 71 | 3,4-dichlorophenyl | 4-oxy | 3-fluoro | pyrrolidin-3(S)-yl | 466 (M + H) |
| 72 | 3,4-dichlorophenyl | 4-oxy | 3-chloro | pyrrolidin-3(S)-yl | 482 (M + H) |
| 73 | 3,4-dichlorophenyl | 4-oxy | 3-bromo | pyrrolidin-3(S)-yl | 526 (M + H) |
| 74 | 3,4-dichlorophenyl | 4-oxy | 3-methoxy | pyrrolidin-3(S)-yl | 478 (M + H) |
| 75 | 3,4-dichlorophenyl | 4-oxy | 3-nitro | pyrrolidin-3(S)-yl | 493 (M + H) |
| 76 | 3,4-dichlorophenyl | 3-oxy | H | pyrrolidin-3(S)-yl | 448 (M + H) |
| 77 | 3,4-dichlorophenyl | 3-oxy | 4-methoxy | pyrrolidin-3(S)-yl | 478 (M + H) |
| 78 | 3,4-dichlorophenyl | 4-oxy | H | cis-4-aminocyclohexyl | 476 (M + H) |
| 79 | 3,4-dichlorophenyl | 4-oxy | 3-fluoro | cis-4-aminocyclohexyl | 494 (M + H) |
| 80 | 3,4-dichlorophenyl | 4-oxy | 3-methoxy | cis-4-aminocyclohexyl | 506 (M + H) |
| 81 | 3,4-dichlorophenyl | 3-oxy | H | cis-4-aminocyclohexyl | 476 (M + H) |
| 82 | 3,4-dichlorophenyl | 3-oxy | 4-methoxy | cis-4-aminocyclohexyl | 506 (M + H) |
| 83 | 3,4-dichlorophenyl | 4-oxy | 3-fluoro | pyrrolidin-3(R)-yl | 567 (M + H) |
| 84 | 3,4-dichlorophenyl | 4-oxy | 3-chloro | pyrrolidin-3(R)-yl | 583 (M + H) |
| 85 | 3,4-dichlorophenyl | 4-oxy | 3-bromo | pyrrolidin-3(R)-yl | 627 (M + H) |
| 86 | 3,4-dichlorophenyl | 4-oxy | 3-methoxy | pyrrolidin-3(R)-yl | 579 (M + H) |
| 87 | 3,4-dichlorophenyl | 4-oxy | 3-nitro | pyrrolidin-3(R)-yl | 594 (M + H) |
| 88 | 3,4-dichlorophenyl | 3-oxy | 4-methoxy | pyrrolidin-3(R)-yl | 579 (M + H) |

EXAMPLE 89

Formulations for pharmaceutical use incorporating compounds of the present invention can be prepared in various forms and with numerous excipients. Examples of such formulations are given below.

| Tablets/Ingredients | Per Tablet |
|---|---|
| 1. Active ingredient (Cpd of Form. I) | 40 mg |
| 2. Corn Starch | 20 mg |
| 3. Alginic acid | 20 mg |
| 4. Sodium Alginate | 20 mg |
| 5. Mg stearate | 1.3 mg |
| | 2.3 mg |

Step 1 Blend ingredients No. 1, No. 2, No. 3 and No. 4 in a suitable mixer/blender.

Step 2 Add sufficient water portion-wise to the blend from Step 1 with careful mixing after each addition. Such additions of water and mixing until the mass is of a consistency to permit its conversion to wet granules.

Step 3 The wet mass is converted to granules by passing it through an oscillating granulator using a No. 8 mesh (2.38 mm) screen.

Step 4 The wet granules are then dried in an oven at 140° F. (60° C.) until dry.

Step 5 The dry granules are lubricated with ingredient No. 5.

Step 6 The lubricated granules are compressed on a suitable tablet press.

Inhalant Formulation

A compound of Formula I, (1 mg to 100 mg) is aerosolized from a metered dose inhaler to deliver the desired amount of drug per use.

Parenteral Formulation

A pharmaceutical composition for parenteral administration is prepared by dissolving an appropriate amount of a compound of formula I in polyethylene glycol with heating. This solution is then diluted with water for injections Ph Eur. (to 100 ml). The solution is then sterilized by filtration through a 0.22 micron membrane filter and sealed in sterile containers.

The above specification and Examples fully disclose how to make and use the compounds of the present invention. However, the present invention is root limited to the particular embodiments described hereinabove, but includes all modifications thereof within the scope of the following claims. The various references to journals, parents and other publications which are cited herein comprise the state of the art and are incorporated herein by reference as though fully set forth.

What is claimed is:

1. A compound of Formula (I):

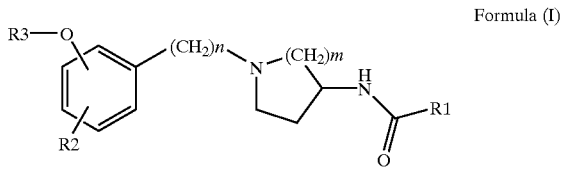

Formula (I)

wherein:

n is 1 or 2;

m is 1 or 2;

R1 is benzofuranyl, naphthyl or phenyl, substituted or unsubstituted with one or two halogen, methyl, trifluoromethyl, methoxy or methylenedioxy groups;

R2 is hydrogen, one or two halogens, methyl, methoxy, nitro or 2,3-(1,3-butadien-1,4-yl);

R3 is 3-dimethylaminopropyl, 2-(pyrrolidin-1-yl)ethyl, 2-(1-morpholino)ethyl, 2-(1-piperazinyl)ethyl, (1-methylpyrrolidin-2(S)-yl)methyl, 1-methylpyrrolidin-3(±)-yl, 1-benzylpiperidin-4-yl, 2(S)-(aminocarbonyl)pyrrolidin-4(S)-yl, pyrrolidin-3(S)-yl, piperidin-4-yl, pyrrolidin-3(R)-yl, or cis-4-aminocyclohexyl;

or a pharmaceutically acceptable salt thereof.

2. A compound of claim 1 wherein $R_1$ is phenyl substituted with one or two halogen, or methyl groups; R2 is hydrogen, halogen, or methoxy; and $R_3$ is 2-(1-piperazinyl)ethyl, pyrrolidin-3(S)-yl, piperidin-4-yl, pyrrolidin-3(R)-yl, 1-methylpyrrolidin-3(±)-yl, or 3-dimethylaminopropyl.

3. A compound of claim 1 chosen from:

3,4-Dichloro-N-{(S)-1-[4-(3-dimethylamino-propoxy)-benzyl]-pyrrolidin-3-yl}-benzamide;

3,4-Dichloro-N-{(R)-1-[4-(3-dimethylamino-propoxy)-benzyl]-pyrrolidin-3-yl}-benzamide;

3,4-Dichloro-N-{1-[4-(3-dimethylamino-propoxy)-benzyl]-piperidin-4-yl}-benzamide;

3,4-Dichloro-N-{(S)-1-[4-iodo-3-(2-piperazin-1-yl-ethoxy)-benzyl]-pyrrolidin-3-yl}-benzamide;

N-{(S)-1-[3-Bromo-4-(1-methyl-pyrrolidin-3-yloxy)-benzyl]-pyrrolidin-3-yl}-3,4-dichloro-benzamide;

4-Bromo-N-{(S)-1-[4-(3-dimethylamino-propoxy)-benzyl]-pyrrolidin-3-yl}-benzamide;

4-Bromo-N-{(R)-1-[4-(3-dimethylamino-propoxy)-benzyl]-pyrrolidin-3-yl}-benzamide;

3,4-Dichloro-N-{(S)-1-[3-(3-dimethylamino-propoxy)-4-iodo-benzyl]-pyrrolidin-3-yl}-benzamide;

3,4-Dichloro-N-{(S)-1-[3-chloro-4-(1-methyl-pyrrolidin-3-yloxy)-benzyl]-pyrrolidin-3-yl}-benzamide 3,4-Dichloro-N-{(S)-1-[2-methoxy-4-(2-piperazin-1-yl-ethoxy)-benzyl]-pyrrolidin-3-yl}-benzamide;

N-{(S)-1-[3-Bromo-4-(piperidin-4-yloxy)-benzyl]-pyrrolidin-3-yl}-3,4-dichloro-benzamide;

N-{(S)-1-[3-Bromo-4-((R)-pyrrolidin-3-yloxy)-benzyl]-pyrrolidin-3-yl}-3,4-dichloro-benzamide;

N-{(S)-1-[3-chloro-4-(piperidin-4-yloxy)-benzyl]-pyrrolidin-3-yl}-3,4-dichloro-benzamide;

3,4-Dichloro-N-((S)-1-{2-[4-(piperidin-4-yloxy)-3-chlorophenyl]-ethyl}-pyrrolidin-3-yl)-benzamide;

3,4-Dichloro-N-((S)-1-{2-[4-(piperidin-4-yloxy)-3-bromophenyl]-ethyl}-pyrrolidin-3-yl)-benzamide;

3,4-Dichloro-N-((S)-1-{2-[3-(piperidin-4-yloxy)-phenyl]-ethyl}-pyrrolidin-3-yl)-benzamide;

3,4-Dichloro-N-((S)-1-{2-[3-(piperidin-4-yloxy)-4-methoxyphenyl]-ethyl}-pyrrolidin-3-yl)-benzamide;

3,4-Dichloro-N-((S)-1-{2-[4-(pyrrolidin-3(S)-yloxy)-3-bromophenyl]-ethyl}-pyrrolidin-3-yl)-benzamide;

3,4-Dichloro-N-((S)-1-{2-[3-(trans-4-aminocyclohexyl)-4-methoxyphenyl]-ethyl}-pyrrolidin-3-yl)-benzamide;

3,4-Dichloro-N-((S)-1-{2-[4-(pyrrolidin-3(R)-yloxy)-3-bromophenyl]-ethyl}-pyrrolidin-3yl)-benzamide;

3,4-Dichloro-N-((S)-1-{2-[4-(pyrrolidin-3(R)-yloxy)-3-nitrophenyl]-ethyl}-pyrrolidin-3-yl)-benzamide;

3,4-Dichloro-N-((S)-1-{2-[3-(pyrrolidin-3(R)-yloxy)-4-methoxyphenyl]-ethyl}-pyrrolidin-3-yl)-benzamide; or 3,4-Dichloro-N-((S)-1-{2-[4-(pyrrolidin-3(R)-yloxy)-3-chlorophenyl]-ethyl}-pyrrolidin-3-yl)-benzamide.

4. A method of treating conditions associated with Urotensin-II imbalance by antagonizing the Urotensin-II receptor which comprises administering to a patient in need thereof, a compound of Formula I of claim 1.

5. A method according to claim 5 wherein the disease is congestive heart failure, stroke, ischemic heart disease, angina, myocardial ischemia, cardiac arrythmias, essential hypertension, pulmonary hypertension, COPD, restenosis, asthma, neurogenic inflammation metabolic vasculopathies, addiction, schizophrenia, impulsivity, anxiety, stress, depression, neuromuscular function, or diabetes.

* * * * *